(12) United States Patent
Cramer et al.

(10) Patent No.: US 7,189,324 B1
(45) Date of Patent: Mar. 13, 2007

(54) HIGH-AFFINITY, LOW MOLECULAR-MASS DISPLACERS FOR ION-EXCHANGE CHROMOTOGRAPHY

(75) Inventors: Steven M. Cramer, Niskayuna, NY (US); James A. Moore, East Greenbush, NY (US); Sun Kyu Park, Daejon (KR); Nihal Tugcu, Franklin Park, NJ (US)

(73) Assignee: Rensselaer Polytechnic Institute, Troy, NY (US)

( * ) Notice: Subject to any disclaimer, the term of this patent is extended or adjusted under 35 U.S.C. 154(b) by 87 days.

(21) Appl. No.: 11/148,887

(22) Filed: Jun. 8, 2005

Related U.S. Application Data

(62) Division of application No. 10/377,080, filed on Feb. 28, 2003, now Pat. No. 6,929,747.

(60) Provisional application No. 60/360,288, filed on Feb. 28, 2002.

(51) Int. Cl.
*B01D 15/08* (2006.01)

(52) U.S. Cl. ............ 210/635; 210/656; 210/659; 210/198.2; 530/413; 530/416; 530/417

(58) Field of Classification Search ........... 210/635, 210/656, 659, 198.2; 530/413, 416, 417
See application file for complete search history.

(56) References Cited

U.S. PATENT DOCUMENTS

| | | | | |
|---|---|---|---|---|
| 5,043,423 A | 8/1991 | Viscomi et al. | ............. | 530/344 |
| 5,427,686 A | 6/1995 | Asher | ............. | 210/635 |
| 5,439,591 A | 8/1995 | Pliura et al. | ............. | 210/635 |
| 5,478,924 A | 12/1995 | Cramer et al. | ............. | 530/416 |
| 5,606,033 A | 2/1997 | Cramer et al. | ............. | 530/416 |
| 6,239,262 B1 | 5/2001 | Cramer et al. | ............. | 530/417 |
| 6,576,134 B1 | 6/2003 | Agner | ............. | 210/635 |

FOREIGN PATENT DOCUMENTS

WO    WO 01/00642 A1    4/2001

OTHER PUBLICATIONS

Cramer et al., Ion-Exchange Displacement Chromatography of Proteins, American Chemical Society, Chapter 3, pp. 28-42 (1993).

(Continued)

*Primary Examiner*—Ernest G. Therkorn
(74) *Attorney, Agent, or Firm*—Heslin Rothenberg Farley & Mesiti, P.C.

(57) ABSTRACT

A method for separating one or more components of a biomolecule mixture by means of an ion exchange chromatographic system operated in the displacement mode includes sequentially perfusing the system with a first solution including the biomolecule mixture, and a second solution including a displacer having a structure selected from formula I and formula II:

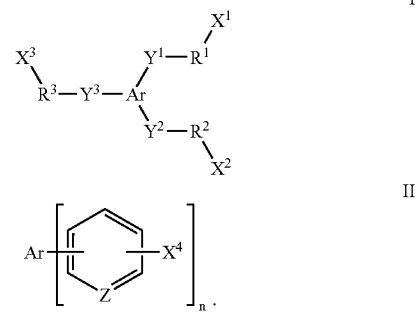

10 Claims, 2 Drawing Sheets

OTHER PUBLICATIONS

Deshmukh et al., Applications of Sample Displacement Techniques to the Purification of Synthetic Oligonucleotides and Nucleic Acids: a Min-Review with Experimental Results, J. of Chromaography A, 806, pp. 77-92 (1998).

Gerstner et al., Take Another Look at Displacement Chromatography, Chemtech, pp. 27-32 (1995).

Gerstner et al., Gram-Scale Purification of Phosphorothioate Oligonucleotides Using Ion-Exchange Displacement Chromatography, Nucleic Acids Research, vol. 23., No. 12, pp. 2292-2299 (1995).

Gerstner et al., Rapid Ion-Exchange Displacement Chromatography of Proteins on Perfusive Chromatography Supports, J. of Chromatography A, 695, pp. 195-204 (1995).

Jayaraman et al., Ion-Exchange Displacement Chromatography of Proteins Dendritic Polymers as Novel Displacers; J. of Chromatography A, 702, pp. 143-155 (1995).

Kalghatgi et al.,Rapid Displacement Chromatography of Melittin on Micropellicular Octadecyl-Silica, J. of Chromatography, 604, pp. 47-53 (1992).

Kundu et al., Protected Amino Acids as Novel Low-Molecular-Weight Displacers in Cation-Exchange Displacement Chromatography, Biotechnology and Bioengineering, vol. 48, pp. 452-460 (1995).

Kundu et al.,Antibodies as Low-Molecular-Mass Displacers in Ion-Echange Chromatography, J. of Chromatography A, 707, pp. 57-67 (1995).

Kundu et al., Low-Molecular-Weight Displacers for High-Resolution Protein Separations, Analytical Biochemistry, 248, pp. 111-116 (1997).

Kundu et al., Displacement Chromatography of Proteins Using Sucrose Octasulfate, BioPharm, pp. 64-68, 70 and 95 (1997).

Patrickios et al., Chromatographic Characterization of Acrylic Polyampholytes, American Chemical Society, Chapter 11, pp. 145-153 (1994).

Shukla et al., Structural Characteristics of Low-Molecular-Mass Displacers for Cation-Exchange Chromatography, J. of Chromatography A, 814 pp. 83-95 (1998).

Shukla et al., Purification of an Antigenic Vaccine Protein by Selective Displacement Chromatography, Biotechnol. Prog., vol. 14, pp. 92-101 (1998).

Skula et al. Purification of Oligonucleotides by High Affinity, Low Molecular Weight Displacers, Biotechnol. Prog, vol. 16, pp. 1064-70 (2000).

HIGH-AFFINITY, LOW MOLECULAR-MASS DISPLACERS FOR ION-EXCHANGE CHROMOTOGRAPHY

CROSS-REFERENCE TO RELATED APPLICATIONS

This application is a division of Ser. No. 10/377,080, filed Feb. 28, 2003, now U.S. Pat. No. 6,929,747, which claims priority from U.S. Provisional Application Ser. No. 60/360,288, filed Feb. 28, 2002, the entire contents of which are incorporated herein by reference.

FEDERALLY SPONSORED RESEARCH

This invention was made with support from NIH Grant GM 47372-O4A2.

FIELD OF THE INVENTION

The invention relates to low molecular weight displacers for separation of biomolecule mixtures by ion exchange chromatography.

BACKGROUND OF THE INVENTION

Interest in biomolecules including proteins and oligonucleotides has exploded in recent years, as evidenced by the rise of the biotechnology industry. These materials are being intensively studied in a variety of ways and for many purposes, ranging from identification of individual components of complex biological mixtures through determination of Quantitative Structure Efficacy Relationships (QSER) to identification of biopharmaceutical drug candidates.

While supplies of raw materials are relatively abundant, an ongoing problem encountered in this work is separation and/or purification of these materials. Chromatographic methods are usually the method of choice, but the separations can be very challenging. Natural sources of biomolecules yield complex mixtures of materials with relatively low concentration of the desired product. Synthetic techniques produce crude products that may be contaminated by closely related impurities, for example, proteins differing in composition by only a few (or even a single) amino acid. Therefore, development of efficient and cost-effective methods for separation and purification of biomolecules is increasingly important.

Displacement chromatography can be used to perform such difficult separations in an efficient and cost effective manner. A particularly attractive feature of displacement chromatography is the ability to concentrate components of a mixture during the separation. Because of this combination of features, the technique is especially appropriate for industrial process-scale chromatography.

The key operational characteristic that distinguishes displacement from step elusion or step gradient chromatography is the use of a displacer compound that has greater affinity for these stationary phase than the desired product. The displacer competes for absorption sites on the stationary phase, causing the feed components to exit the column as adjacent "square wave" zones of highly concentrated pure material, in the order of increasing affinity of absorption. An important distinction between displacement and step gradient chromatography is that the displacer front always remains behind the adjacent feed zones in the displacement train, while, desorbents, for example, salts and organic modifiers, move through the feed zones. The implications of this distinction are quite significant in that displacement chromatography can concentrate and purify components from mixtures having low separation factors, while in the case of desorption chromatography, relatively large separation factors are generally required to give satisfactory resolution.

A limited number of materials for use as displacers in chromatographic systems have been described in the patent and scientific literature. These include large polyelectrolytes as displacers for separation of proteins in ion exchange systems. In addition, several types of low-molecular weight displacers for ion exchange have also been described. (See, for example, U.S. Pat. Nos. 5,478,924; 5,606,033 and 6,239,262). Low-molecular weight displacers have significant operational advantages as compared to large polyelectrolyte displacers. First and foremost, if there is any overlap between the displacer and the protein of interest, these low-molecular weight materials can be readily separated from the purified protein during post-displacement processing using standard size-based purification methods, for example, size exclusion chromatography and/or ultra filtration. This advantage is particularly important for meeting FDA standards for validating displacement chromatic graphic bioprocesses. The salt dependent adsorption behavior of these low-molecular weight displacers greatly facilitates column regeneration. Finally, the use of low-molecular weight displacers enables the operation of displacements in the selective displacement mode which can result in elution of the weakly retained proteins in the induced salt gradient, displacement of the bioproduct of interest and closely related impurities, and desorption of the more strongly retained impurities after breakthrough of the displacer front.

However, the major obstacle to the implementation of displacement chromatography has been a lack of displacer molecules for particular separations. Therefore, there is a continuing need for additional displacer compounds that have high affinity for the stationary phase of ion exchange chromatographic systems, as well as chemically selective displacers for specific separations.

SUMMARY OF THE INVENTION

It has been unexpectedly discovered that displacers having the structure of formula I or formula II have high affinity for ionic exchange stationary phase materials.

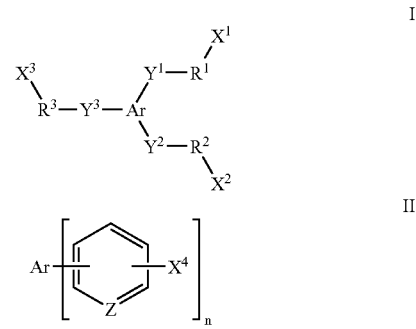

Because of this high affinity, these displacers can be very effectively used for purification or separation of biomolecules such as proteins and oligonucleotides.

Accordingly, the present invention relates to a method for separating one or more components of a biomolecule mixture by means of an ion exchange chromatographic system operated in the displacement mode. The separation is performed by sequentially perfusing the system with a first solution including the biomolecule mixture, and a second solution including a displacer having a structure selected from formula I and formula II.

DETAILED DESCRIPTION OF THE INVENTION

Figure 1:
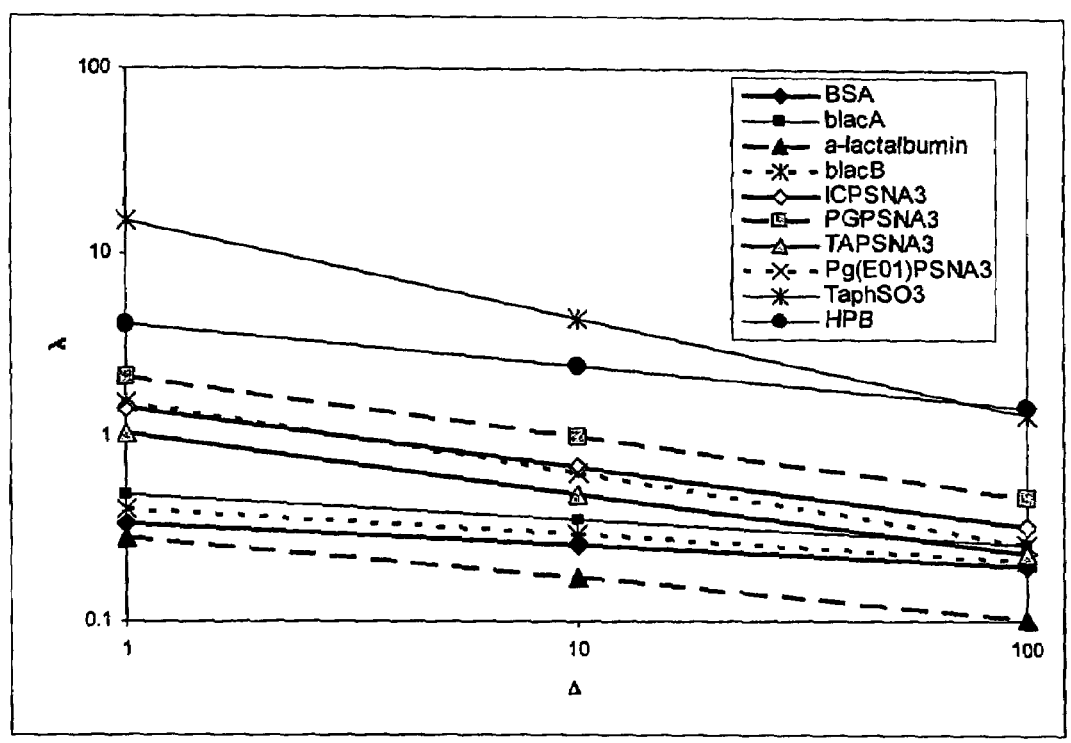
FIG. 1 is a ranking of dynamic affinities of displacers on Source 15Q stationary phase.

The present invention relates to a method for separating one or more components of a biomolecule mixture by means of an ion exchange chromatographic system operated in the displacement mode. The method includes sequentially perfusing the system with a first solution including the biomolecule mixture, and a second solution including a displacer. The displacer is an ion having a structure selected from formula I and formula II:

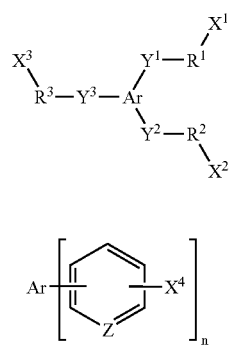

wherein Ar is phenyl, naphthalenyl, phenanthrenyl, anthracenyl, perylenyl, pyrenyl, fluorenyl, triazolyl, carbazolyl, indolyl, benzocarbazolyl, acridinyl, phenothiazinyl, or thianthrenyl;

$R^1$, $R^2$, and $R^3$ are independently alkyl, aryl, heteroalkyl, alkylaryl, oxaalkyl, oxaaryl, oxaalkylaryl, substituted alkyl, substituted aryl, substituted alkylaryl, substituted oxaalkyl, substituted oxaaryl, substituted oxaalkylaryl or a direct bond; and at least one of $R^1$, $R^2$, and $R^3$ is other than a direct bond;

$X^1$, $X^2$, and $X^3$ are independently hydrogen, $X^5$ or $X^6$; and at least one of $X^1$, $X^2$, and $X^3$ is other than hydrogen $X^4$ is sulfonate, sulfate, phosphate, carboxylate, tertiary amino or quaternary amino;

$X^5$ is sulfonate, sulfate, phosphate, or carboxylate;

$X^6$ is tertiary amino or quaternary amino;

$Y^1$, $Y^2$, and $Y^3$ are independently O, S or a direct bond; and Z is CH or N; and n is an integer from 1 to 6.

In formula I, the Ar group may be mono-, di-, or trisubstituted as specified above, that is, substituted with one or more of the groups $Y^1R^1X^1$, $Y^2R^2X^2$, and $Y^3R^3X^3$. In formula II, the Ar group may be substituted with up to six aryl or heteroaryl groups, each having an ionic substitutent selected from sulfonate, sulfate, phosphate, carboxylate, tertiary amino and quaternary amino.

The counterion(s) for the displacer ion of formula is(are) not critical, and may be any appropriately charged ion. For example, a preferred counterion for negatively charged displacers of formula I or II is Na⁺.

In one embodiment, the displacers of formula I are trisubstituted phenyl or triazolyl derivatives. Preferred groups for $R^1$, $R^2$, and $R^3$ are alkyl, aryl, and oxaalkyl. Examples of displacers of formula I are:

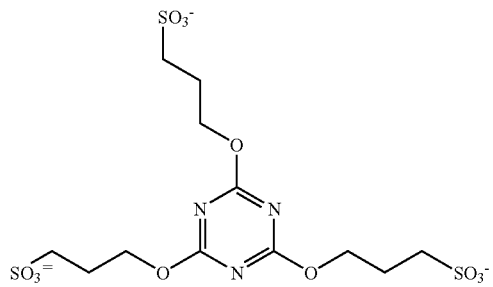

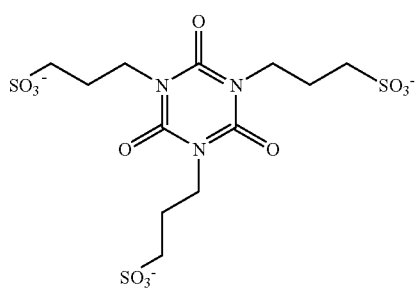

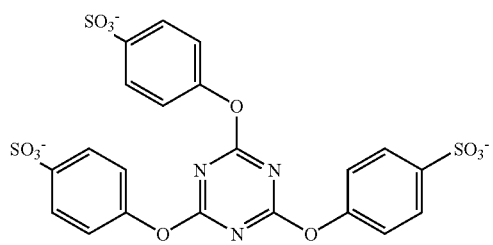

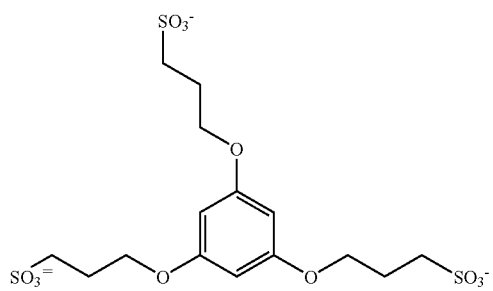

-continued

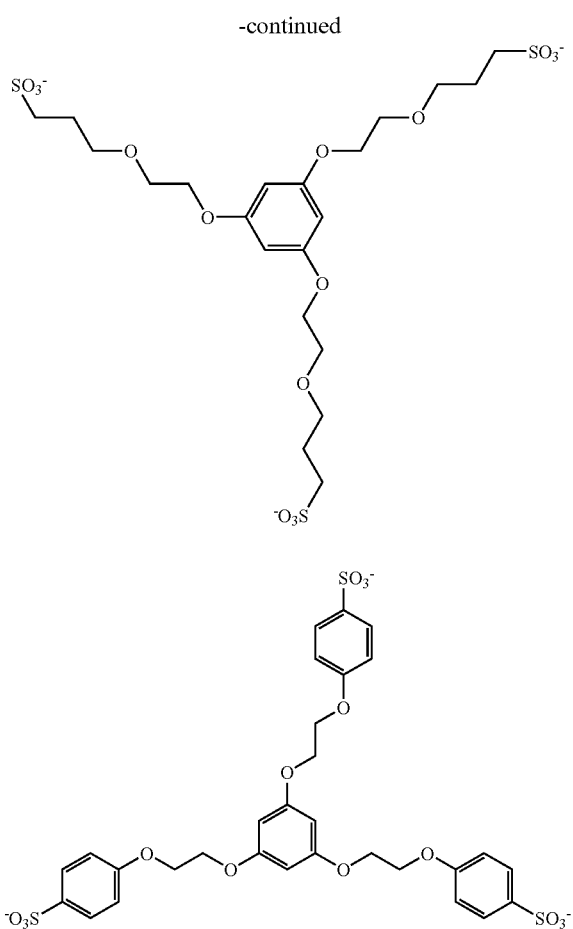

In another embodiment, displacers of formula II are phenyl derivatives, that is, Ar is phenyl. Preferred substituents are also phenyl. A particularly preferred displacer is:

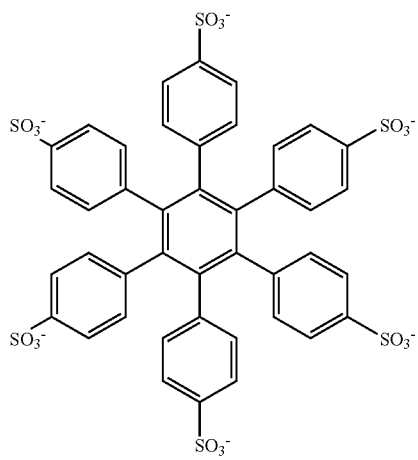

Components of the biomolecule mixture include at least one biomolecule, for example, biological macromolecules, such as proteins or oligonucleotides, or other naturally occurring molecules such as peptides, viruses or vaccines. Proteins differ from peptides in molecular weight. In the context of the present invention, peptides are defined as having molecular weight of less than 10,000 Daltons, while proteins have molecular weight of greater than 10,000 Daltons.

The biomolecule mixture to be separated typically contains one type of biomolecule, such as a mixture of closely related proteins or oligonucleotides. If desired, mixtures containing complex mixtures of different types of compounds may also be separated.

Separation of a component of the mixture yields that component in a form containing fewer impurities than in the starting mixture. One aspect of separating a component of a biomolecule mixture is purifying that component, and, in one embodiment, the method of the present invention may be used to purify a biomolecule. In this embodiment, the separation typically yields a product of at least 90% purity, and the purity may be as high as 99%. The method is particularly useful when the desired biomolecule is contaminated with a closely related impurity which is difficult to remove by conventional methods. However, the impurity (ies) may be any unwanted contaminant of the biomolecule to be purified, including low molecular weight materials.

Conventional hardware systems may be used for the separation, including components such as a column, pump, and detector, with minor modifications to enable the sequential perfusion of the column with the carrier, feed, displacer, and regenerant solutions (Shukla A. A. and Cramer S. M; *Bioseparations by Displacement Chromatography*, in Ahuja (ed.); *Handbook of Bioseparations*; Academic Press; accepted for publication; Frenz, J. and Horvath, Cs., *High Performance Chromatography-Advances and Perspectives*, in: Cs. Horvath (ed.), *High Performance Displacement Chromatography*; Vol. 5; Academic Press (1988)). The IEX system also includes a stationary phase and a mobile phase, as in conventional systems.

Suitable matrix materials for the stationary phase include those based on agarose, polymethylmethacrylate, hydrophilized polystyrene-divinylbenzene, dextran, or cellulose. In chromatographic systems for separating negatively charged species, the matrix is typically functionalized with a cationic group, such as a quaternary amine group. Negatively charged displacers, that is, those bearing sulfonate, sulfate, phosphate, or carboxylate functionality, are used with a cationic stationary phase. In systems, for separating positively charged species, the matrix is typically functionalized with an anionic group, such as a sulfonate group. Positively charged displacers, that is, those bearing tertiary amino or quaternary amino functionality, are used with an anionic stationary phase.

The mobile phase is typically also a conventional one, usually a buffered aqueous solution. The mobile phase is used as the carrier solution, as the solvent for the biomolecule mixture in the feed solution, and as the solvent for the displacer in the displacer solution. The regenerant solution also includes the mobile phase, and may have additional solvents to facilitate removal of the displacer from the system.

In performing a separation according to the method of the present invention, the IEX system is operated in displacement mode. Displacement mode differs from conventional elution or step gradient modes primarily in that a displacer is passed through the column behind or after the sample. When operated in displacement mode, the system is sequentially perfused with a first or feed solution including the biomolecule mixture, and a second or displacer solution including the displacer. If desired, the system may be equilibrated with the carrier solution before beginning perfusion of the feed solution. After the separation, it is usually desirable to regenerate the column by removing the displacer from the system. This may be done by passing a regenerant solution through the column. Displacers useful in the methods of the present invention are typically removed from the column after washing with from five to twenty column volumes of the regenerant solution, although, in some cases, use of much more or much less solution may be desirable. The composition of the regenerant solution is typically optimized for a particular displacement, and may contain organic solvents in addition to the mobile phase aqueous solution.

In the context of the present invention, alkyl is intended to include linear, branched, or cyclic hydrocarbon structures and combinations thereof. Lower alkyl refers to alkyl groups of from 1 to 4 carbon atoms. Lower alkyl groups include methyl, ethyl, n-propyl, isopropyl, and n-, s- and t- butyl. Preferred alkyl groups are those of $C_{20}$ or below. Cycloalkyl is a subset of alkyl and includes cyclic hydrocarbon groups of from 3 to 8 carbon atoms. Examples of cycloalkyl groups include cyclopropyl, cyclobutyl, cyclopentyl, and norbornyl Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, and cyclohexyloxy. Lower alkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, and benzyloxycarbonyl. Lower-acyl refers to groups containing one to four carbons.

Aryl and heteroaryl mean a 5- or 6-membered aromatic or heteroaromatic ring containing 0–3 heteroatoms selected from nitrogen, oxygen or sulfur; a bicyclic 9- or 10-membered aromatic or heteroaromatic ring system containing 0–3 heteroatoms selected from Nitrogen, oxygen or sulfur; or a tricyclic 13- or 14-membered aromatic or heteroaromatic ring system containing 0–3 heteroatoms selected from Nitrogen, oxygen or sulfur. Each of these rings is optionally substituted with 1–3 lower alkyl, substituted alkyl, substituted alkynyl, carbonyl, nitro, halogen, haloalkyl, hydroxy, alkoxy, $OCH(COOH)_2$, cyano, primary amino, secondary amino, acylamino, phenyl, benzyl, phenoxy, benzyloxy, heteroaryl, or heteroaryloxy; each of said phenyl, benzyl, phenoxy, benzyloxy, heteroaryl, and heteroaryloxy is optionally substituted with 1–3 substituents selected from lower alkyl, alkenyl, alkynyl, halogen, hydroxy, haloalkyl, alkoxy, cyano, phenyl, benzyl, benzyloxy, carboxamido, heteroaryl, heteroaryloxy, nitro or —NRR (wherein R is independently H, lower alkyl or cycloalkyl, and —RR may be fused to form a cyclic ring with nitrogen). The aromatic 6- to 14-membered carbocyclic rings include, for example, benzene, naphthalene, indane, tetralin, and fluorene; and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Alkylaryl means an alkyl residue attached to an aryl ring. Examples are benzyl and phenethyl. Heteroarylalkyl means an alkyl residue attached to a heteroaryl ring. Examples include pyridinylmethyl and pyrimidinylethyl.

Heterocycle means a cycloalkyl or aryl residue in which one to two of the carbons is replaced by a heteroatom such as oxygen, nitrogen or sulfur. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, and tetrahydrofuran.

Substituted alkyl, aryl, cycloalkyl, or heterocyclyl refer to alkyl, aryl, cycloalkyl, or heterocyclyl wherein up to three H atoms in each residue are replaced with halogen, haloalkyl, hydroxy, lower alkoxy, carboxy, carboxalkoxy, carboxamido, cyano, carbonyl, nitro, primary amino, secondary amino, alkylthio, sulfoxide, sulfone, acylamino, acyloxy, amidino, phenyl, benzyl, heteroaryl, phenoxy, benzyloxy, heteroaryloxy, or substituted phenyl, benzyl, heteroaryl, phenoxy, benzyloxy, or heteroaryloxy.

Haloalkyl refers to an alkyl residue, wherein one or more H atoms are replaced by halogen atoms; the term haloalkyl includes perhaloalkyl. Examples of haloalkyl groups that fall within the scope of the invention include $CH_2F$, $CHF_2$, and $CF_3$.

Oxaalkyl refers to an alkyl residue in which one or more carbons have been replaced by oxygen and attached to the parent structure through an oxygen. Examples include methoxypropoxy, 3,6,9-trioxadecyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups. Similarly, thiaalkyl and azaalkyl refer to alkyl residues in which one or more carbons has been replaced by sulfur or nitrogen, respectively. Examples include ethylaminoethyl and methylthiopropyl.

Anionic displacers of formula I may be synthesized by the methods illustrated in Schemes 1 and 2.

SCHEME 1
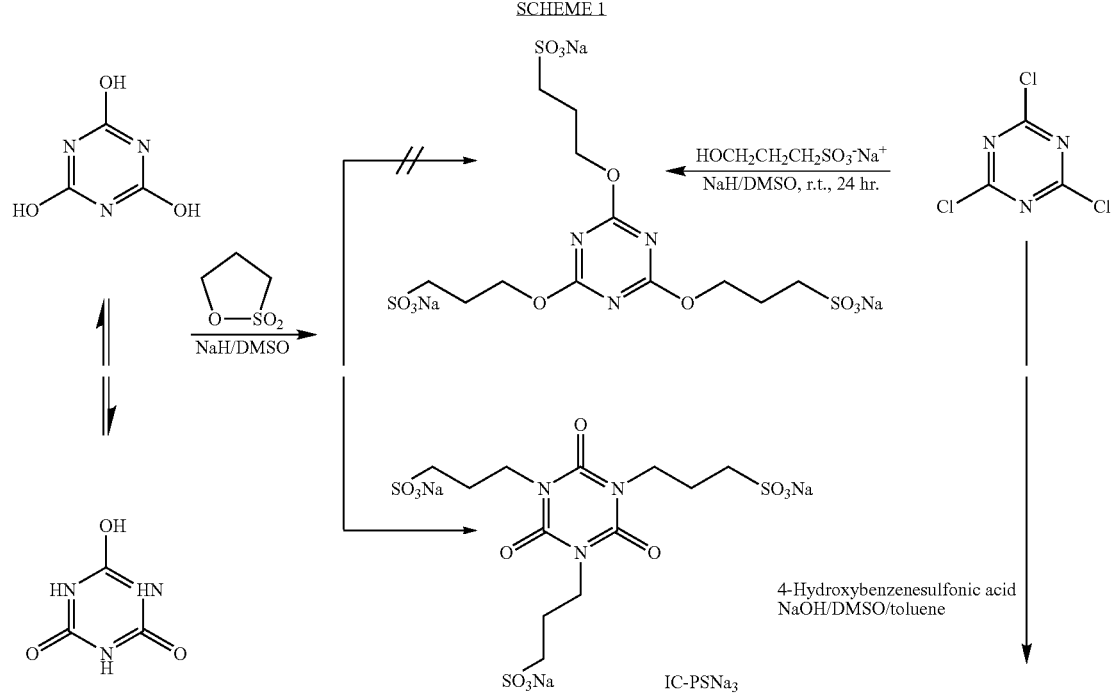
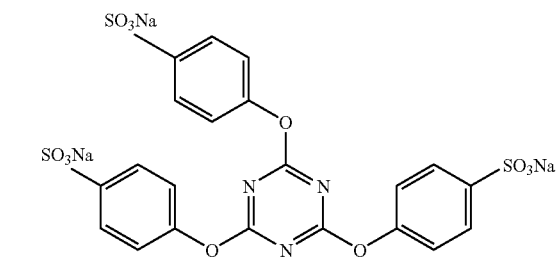
TA-PhSO$_3$Na
SCHEME 2
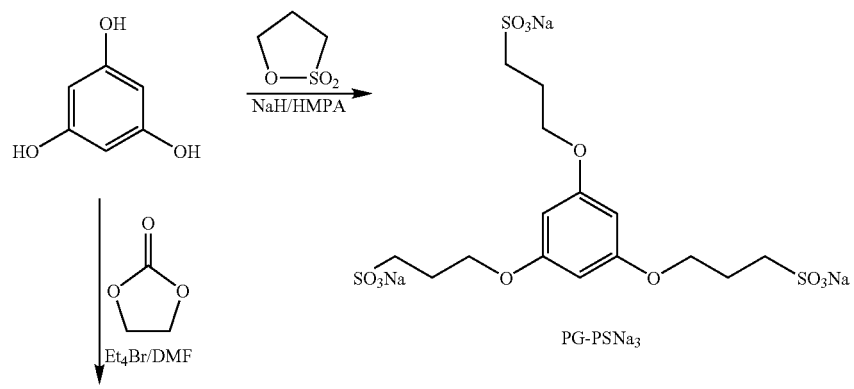
PG-PSNa$_3$

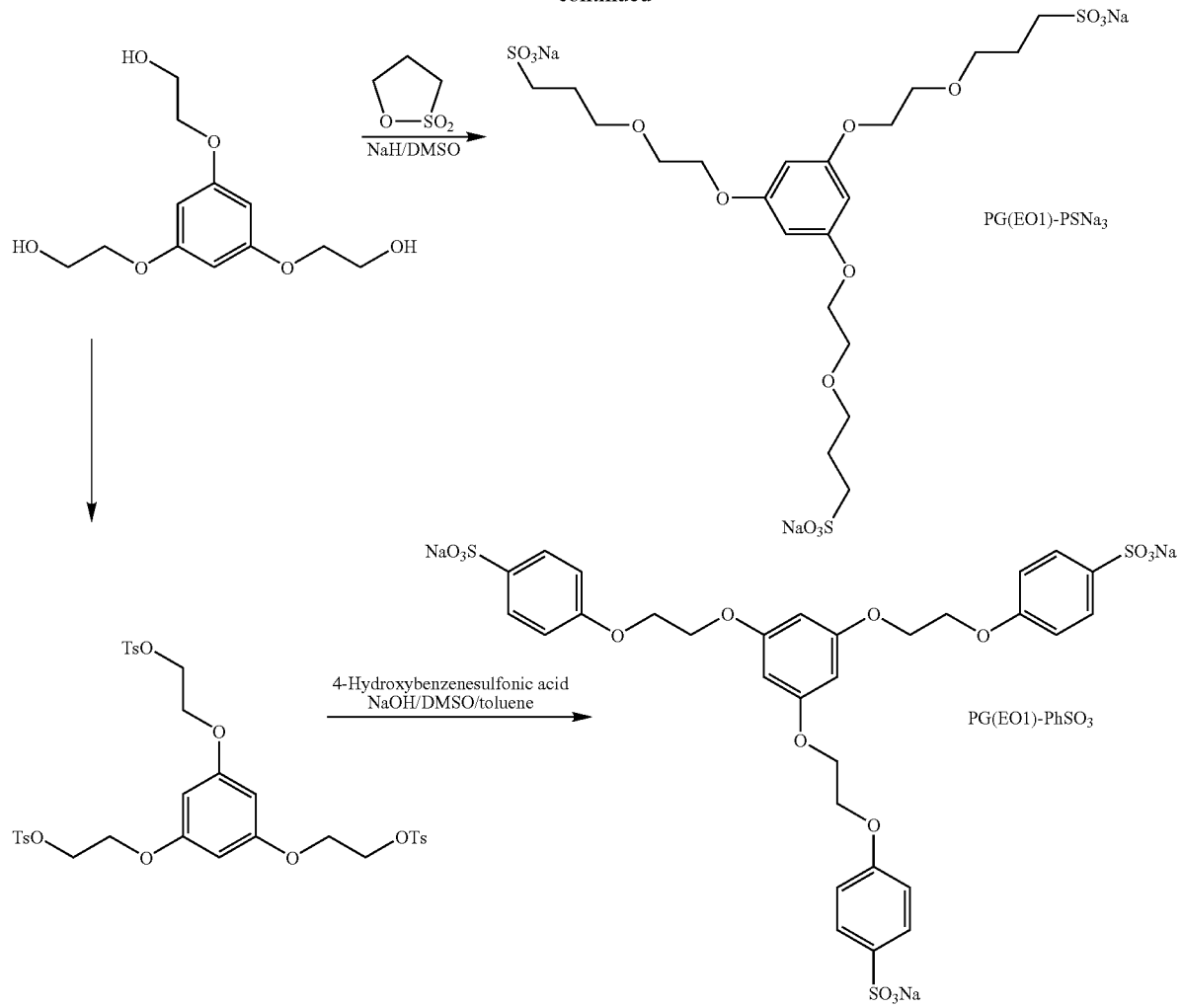
Anionic displacers of formula II, where n=6, may be synthesized by the method illustrated in Scheme 3.
SCHEME 3
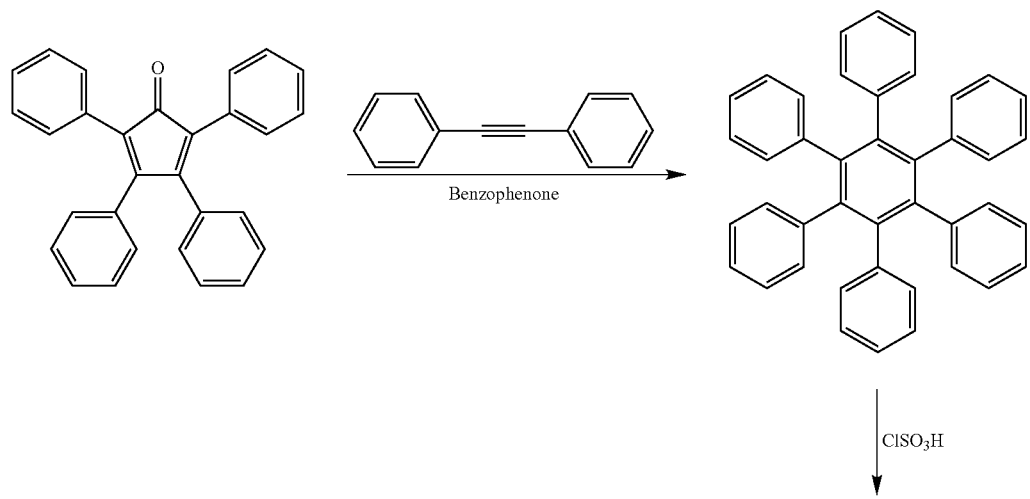

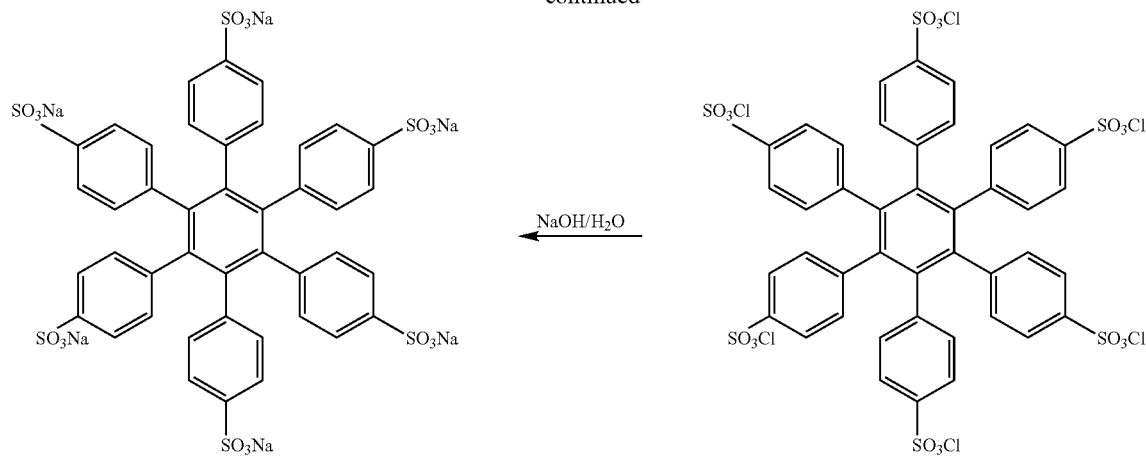

-continued

Where n<6, the displacers may be prepared by functionalizing commercially available starting materials, such as biphenyl or terphenyl.

Cationic displacers may be synthesized by similar methods. While Schemes 1, 2 and 3 show preparation of anionic displacers having sulfonate ionic substituents, cationic displacers having amino substituents are readily synthesized by modification of the functionalization step(s). Methods for functionalizing an aromatic ring with a tertiary or quaternary amine are known in the art.

The following examples illustrate preparation of displacers having the structure of formulas I and II, use of these displacers to separate closely related proteins in an anionic IEX system, and the results of screening experiments that indicate that the displacers are also effective for separation of oligonucleotides.

EXAMPLES

Example 1

Synthesis of Displacers

IC—PS $Na_3$: To a suspension of sodium hydride of 95% purity (1.80 g, 0.07 mol) in anhydrous DMSO (50 mL) was added cyanuric acid (2.64 g, 0.02 mol) in anhydrous DMSO (50 mL) dropwise at room temperature under an argon atmosphere. After the addition of cyanuric acid (1,3,5-triazine-2,4,6-triol), the reaction mixture was stirred at 80° C. for 1 hr. The temperature of the reaction mixture was lowered to 50° C. and then 1,3-propane sultone (10 g, 0.08 mol) in anhydrous DMSO (30 mL) was added dropwise to the suspension. At this temperature, the reaction mixture was stirred for 1 day. As the reaction proceeded, the suspension became yellowish in color. Finally the reaction mixture was stirred at 80° C. for one hour. After cooling to room temperature, the reaction mixture was filtered. THF (300 mL) was added to the resulting solution while stirring. The resultant white precipitate was filtered, and dried in a vacuum oven at 60° C. For further purification, the white product was placed in 400 mL of methanol and the suspension was boiled until the suspension was concentrated to 200 mL. After cooling to room temperature, the white solid was filtered, and dried in a vacuum oven at 110° C. for 3 days to afford 7.9 g of IC—$PSNa_3$ in a yield of 70%. $^1H$ NMR (DMSO-$d_6$): δ 3.77 (t, —NC$\underline{H}_2$CH$_2$CH$_2$SO$_3$Na, 6H), 2.47 (t, —NCH$_2$CH$_2$C$\underline{H}_2$SO$_3$Na, 6H), 1.87 (quintet, —NCH$_2$C$\underline{H}_2$CH$_2$SO$_3$Na, 6H). $^{13}$C NMR (DMSO-$d_6$): δ 149.01 (—N—$\underline{C}$=O), 48.94 (—N$\underline{C}$H$_2$CH$_2$CH$_2$SO$_3$Na), 41.82 (—NCH$_2$CH$_2$$\underline{C}$H$_2$SO$_3$Na), 23.73 (—NCH$_2$$\underline{C}$H$_2$CH$_2$SO$_3$Na). IR (KBr): 1681 (vs, C=O), 1472 (s), 1206 (s), 1058 (s), 764, 613, 531 cm$^{-1}$.

PG-$PSNa_3$: To a suspension of sodium hydride of 95% purity (1.07 g, 0.04 mol) in anhydrous HMPA (40 mL) was added phloroglucinol (1.53 g, 0.01 mol) dropwise at room temperature under an argon atmosphere. The reaction mixture was stirred at room temperature for 5 hr. 1,3-Propane sultone (5.18 g, 0.04) in HMPA (20 mL) was added dropwise to the suspension and the reaction mixture was stirred at room temperature for 12 hr. The temperature of the reaction mixture was raised to 80° C. and the mixture was stirred for 12 hr. After cooling to room temperature, the reaction mixture was filtered. The solution was poured into a mixture of ethanol/acetone (100 mL/400 mL). The resultant precipitate was filtered, washed with ethanol and acetone, and dried in a vacuum oven at 60° C. To purify further, the product was placed in 300 mL of methanol and the suspension was boiled and concentrated to 150 mL. After cooling to room temperature, the white solid was filtered, and dried in a vacuum oven at 100° C. for 2 days to afford 5.0 g of PG-$PSNa_3$ in a yield of 74%. $^1H$ NMR (DMSO-$d_6$): δ 6.04 (s, aromatic protons, 3H), 3.98 (t, —OC$\underline{H}_2$CH$_2$CH$_2$SO$_3$Na, 6H), 2.55 (t, —OCH$_2$CH$_2$C$\underline{H}_2$SO$_3$Na, 6H), 1.97 (quintet, —OCH$_2$C$\underline{H}_2$CH$_2$SO$_3$Na, 6H). $^{13}$C NMR (DMSO-$d_6$): δ 160.47 (aromatic $\underline{C}$—OCH$_2$—), 93.75 (aromatic $\underline{C}$—H), 66.66 (—O$\underline{C}$H$_2$CH$_2$CH$_2$SO$_3$Na), 47.92 (—OCH$_2$CH$_2$$\underline{C}$H$_2$SO$_3$Na), 25.18 (—OCH$_2$$\underline{C}$H$_2$CH$_2$SO$_3$Na).

TA-$PSNa_3$: To a suspension of sodium hydride of 95% purity (1.82 g, 0.072 mol) in anhydrous DMSO (200 mL) was added 3-hydroxy-1-propanesulfonic acid sodium salt (11.50 g, 0.056 mol) in three portions at room temperature under an argon atmosphere. The reaction mixture was stirred at room temperature for 8 hr. Cyanuric chloride (2,4,6-trichloro-1,3,5-triazine, 3.000 g, 0.016 mol) was added to the suspension in three portions and then the reaction mixture was stirred at room temperature for one day. As the reaction proceeded, the reaction mixture became yellowish in color. The reaction mixture was filtered to remove some salt. The resulting solution was poured into acetone (300 mL) with stirring. The white precipitate was filtered, and dried in a vacuum oven at 60° C. For further purification, the product was recrystallized from water/ethanol (1/4). The white solid was filtered, and dried in a vacuum oven at 110° C. for 3 days to afford 4.0 g of TA-PSNa$_3$ in a yield of 48%. $^1$H NMR (DMSO-d$_6$): δ 4.20 (t, —OC$\underline{H}_2$CH$_2$CH$_2$SO$_3$Na, 6H), 2.53 (t, —OCH$_2$CH$_2$C$\underline{H}_2$SO$_3$Na, 6H), 1.91 (quintet, —OCH$_2$C$\underline{H}_2$CH$_2$SO$_3$Na, 6H). $^{13}$C NMR (DMSO-d$_6$): δ 172.01 (—N=$\underline{C}$—O—), 64.37 (—O$\underline{C}$H$_2$CH$_2$CH$_2$SO$_3$Na), 47.91 (—OCH$_2$CH$_2$$\underline{C}$H$_2$SO$_3$Na), 24.98 (—OCH$_2$$\underline{C}$H$_2$CH$_2$SO$_3$Na).

1,3,5-Tris(2-hydroxyethoxy)benzene: A mixture of phloroglucinol (12.60 g, 0.10 mol), ethylene carbonate (35 g, 0.39 mol), and tetraethylammonium bromide (8 g, 0.04 mol) in DMF (20 mL) was heated at 150° C. for 14 hr. After evaporating the solvent, the residue was purified on a silica gel chromatography column using a mixture of methylene chloride and acetonitrile: 1/1, 1/2, 1/3 and 1/4 as eluents to give 9.6 g of 1,3,5-tris(2-hydroxyethoxy)benzene (37% yield). The product was purified further by recrystallization from cold methylene chloride and THF to afford 5.5 g (21%). $^1$H NMR (DMSO-d$_6$): δ 6.08 (s, aromatic protons, 3H), 4.83 (s, OH, 3H), 3.92 (t, —OC$\underline{H}_2$—, 6H), 3.69 (m, —C$\underline{H}_2$OH, 8H). $^{13}$C NMR (DMSO-d$_6$): δ 160.54 (aromatic $\underline{C}$—O—), 93.81(aromatic $\underline{C}$—H), 69.53 (—C$\underline{H}_2$O—), 59.55 (—$\underline{C}$H$_2$OH). FT-IR (KBr, m$^{-1}$): 3255 (OH), 2947, 2371, 1596, 1462, 1377, 1167, 1071, 1024, 902, 745.

1,3,5-Tris(3-tosyloxy-1-oxapropyl)benzene: To a solution of 1(3.0 g, 12.00 mmol) in pyridine (30 mL) was added p-toluensulfonylchloride (11.40 g, 60 mmol) in pyridine (30 mL) dropwise at 0° C. under nitrogen. The reaction mixture was stirred at 0–20° C. for 1 day. The resulting salt was filtered and then two thirds of the pyridine was distilled under vacuum at room temperature. Into the resulting solution was poured ice/water with stirring. The precipitate was filtered and dried under vacuum at room temperature, overnight. The product was dissolved in chloroform, dried over magnesium sulfate, and the solid was filtered. After one half the solvent in the filtrate was removed on a rotary evaporator, methanol was added to the solution until the volume ratio of both solvents reached approximately one to one. The mixture was allowed to stand overnight in the refrigerator to initiate precipitation. The resulting solid was filtered and dried in a vacuum oven at 60° C. overnight to give 6.5 g of 1,3,5-tris(3-tosyloxy-1-oxapropyl)benzene (75% yield). $^1$H NMR (DMSO-d$_6$): δ 7.81 (d, 6H), 7.47 (d, 6H); protons on the phenyl moiety of the tosyl group, 5.99 (s, protons on the phenyl moiety of the phloroglucinoxy group, 3H), 4.31 (t, PhOC$\underline{H}_2$CH$_2$O—, 6H), 4.09 (t, PhOCH$_2$C$\underline{H}_2$O—, 6H), 2.40 (s, —CH$_3$, 9H).

PG(EO1)-PSNa$_3$: To a suspension of NaH (0.31 g, 12.40 mmol) in anhydrous DMSO (20 mL), 1,3,5-tris(2-hydroxyethoxy)benzene (0.80 g, 3.10 mmol) was added slowly at room temperature under nitrogen. The mixture was stirred for 4 hours. 1,3-Propane sultone (1.90 g, 15.49 mmol) was added to the suspension at room temperature and then the reaction mixture was heated at 80° C. for 1 day. The reaction mixture was cooled to room temperature and poured into isopropanol. The resulting precipitate was filtered and dried under vacuum at 60° C. overnight. The product was purified further by fractional precipitation from DMSO by adding increasing amounts of ethanol. The first precipitate was filtered and the second was collected taken from ethanol and dried in a vacuum oven at 60° C. overnight. Finally, the product was purified further by precipitation from DMSO/ethanol/water to give 0.7 g of PG(EO1)-PSNa$_3$ (51% yield). m.p.=253° C. (by DSC). $^1$H NMR (DMSO-d$_6$): δ 6.11(s, aromatic H, 3H), 4.03 (t, PhOC$\underline{H}_2$—, 6H), 3.65 (t, —OCH$_2$C$\underline{H}_2$OCH$_2$—, 6H), 3.49 (t, —OC$\underline{H}_2$CH$_2$CH$_2$—), 2.48 (t, —C$\underline{H}_2$SO$_3$Na, 6H), 1.81 (quintet, —OCH$_2$C$\underline{H}_2$CH$_2$—, 6H). $^{13}$C NMR (DMSO-d$_6$): δ 160.34 (aromatic $\underline{C}$—OH), 93.86 (aromatic $\underline{C}$—H), 69.65 (PhO$\underline{C}$H$_2$—), 68.47 (—O$\underline{C}$H$_2$CH$_2$OCH$_2$—), 67.18 (—OCH$_2$CH$_2$O$\underline{C}$H$_2$—), 48.24 (—$\underline{C}$H$_2$SO$_3$Na), 25.60 (—OCH$_2$$\underline{C}$H$_2$CH$_2$—).

PG(EO1)-PhSO$_3$Na: 4-Hydroxybenzenesulfonic acid sodium salt dihydrate (2.18 g, 9.40 mmol), sodium hydroxide (0.36 g, 8.95 mmol) in DMSO (25 mL) and HMPA (10 mL) were placed in a 2-neck-round bottom flask equipped with a Dean-Stark trap and condenser under nitrogen. The reaction mixture was heated at 130–140° C. while adding and distilling toluene several times for 1 day to generate anhydrous phenoxide ions. The mixture was cooled to room temperature. To the suspension was added 1,3,5-tris(3-tosyloxy-1-oxapropyl)benzene (1.50 g, 2.08 mmol) and then the temperature was raised to 80° C. and stirred for 1 day. After cooling to room temperature, the reaction mixture was poured into isopropyl alcohol with stirring. The resulting precipitate was filtered and dried in a vacuum oven at 60° C. overnight. The product was purified further by reprecipitation from water and isopropyl alcohol, and the obtained product was dried in a vacuum oven at 60° C. for 2 days to give 1.50 g (91% yield) of PG(EO1)-PhSO$_3$Na. m.p.=333° C. (on DSC). $^1$H NMR (DMSO-d$_6$): δ 7.55(d, ortho-protons to the sulfonyl group, 6H), 6.92 (d, meta-proton to the sulfonyl group, 6H), 6.23 (s, protons on the phenyl ring of phloroglucinoxy group, 3H), 4.29 (br.s, —OC$\underline{H}_2$C$\underline{H}_2$O—, 12H). $^{13}$C NMR (DMSO-d$_6$): δ 160.24 (para-carbon to the sulfonyl group), 158.36 (aromatic $\underline{C}$—O of the phloroglucinoxy group), 141.11($\underline{C}$—SO$_3$Na), 127.14 (ortho-carbon to the sulfonyl group), 113.37 (meta-carbon to the sulfonyl group), 94.15 (aromatic $\underline{C}$—H of the phloroglucinoxy group), 66.43, 66.37 (—O$\underline{C}$H$_2$$\underline{C}$H$_2$O—).

TA-PhSO$_3$Na: 4-Hydroxybenzenesulfonic acid sodium salt dihydrate (4.00 g, 16.90 mmol) and sodium hydroxide (0.67 g, 16.46 mmol) in DMSO (60 mL) were placed in a 2-neck-round bottom flask equipped with a Dean-Stark trap and a condenser under nitrogen. The reaction mixture was heated at 130–140° C. while adding and distilling toluene several times for one-day to generate anhydrous phenoxide ion. The mixture was cooled to room temperature. To the suspension was added cyanuric chloride (0.70 g, 3.79 mmol) slowly with stirring at room temperature for one-day. The resulting precipitate was filtered and dried in a vacuum oven at 60° C. overnight. The product was precipitated from ethanol and the obtained product was filtered and dried in a vacuum oven at 60° C. for one-day. The white solid was purified further by reprecipitation from the water, DMSO ethanol mixture to give 1.40 g (56%) of TA-PhSO$_3$Na m.p.=440° C. (by DSC). $^1$H NMR (DMSO-d$_6$): δ 7.68(d, ortho-proton to the sulfonyl group, 6H), 7.22(d, meta-proton to the sulfonyl group, 6H). $^{13}$C NMR (DMSO-d$_6$): δ 173.06 (carbon atom of the triazine ring), 151.32 (para-carbon atom to the sulfonyl group), 145.98 ($\underline{C}$—SO$_3$Na), 127.03(ortho-carbon atom to the sulfonyl group), 120.75 (meta-proton to the sulfonyl group).

1,4 Hexaphenylbenzene: A mixture of tetraphenylcyclopentadienone (8.0 g, 21.0 mmol), diphenylacetylene (8.0 g, 43.0 mmol), and benzophenone (40 g) was heated at 320° C. for one-hour in a one-neck round bottom flask attached to an air condenser. The reaction mixture was cooled to room temperature to give a crystalline precipitate which was filtered, washed with benzene and dried in a vacuum oven at 80° C. overnight. The product was purified further by recrystallization from diphenylether, filtered and washed with hot benzene to give 8.1 g of 1,4 hexaphenylbenzene (72%). $^1$H NMR (THF-d$_8$): δ 6.81–6.75 (m, C—H, 30H). $^{13}$C NMR (THF-d$_8$): δ 141.88 (core phenyl group-C of the substituted phenyl group), 141.60 (carbon atom of the core phenyl group), 132.50 (meta-carbon of substituted phenyl group), 127.53 (para-carbon atom of the substituted phenyl group), 126.09 (ortho-carbon of substituted phenyl group).

HPB—SO$_3$Na: To 1,4 hexaphenylbenzene (4.0 g, 7.50 mmol) was added chlorosulfonic acid (45 mL) slowly at room temperature and the reaction mixture was stirred overnight. The solution was poured into ice/water and the resulting precipitate was filtered and dried in a vacuum oven at 60° C. to give 8.0 g (95%) of hexaphenylbenzene hexasulfonyl chloride. The product was used in the next step without further purification.

To a solution of sodium hydroxide (4.55 g, 113.80 mmol) in water (100 mL) was added hexaphenylbenzene hexasulfonyl chloride (8.0 g, 7.10 mmol) at room temperature. The reaction mixture was heated at 50° C. overnight. After cooling to room temperature, the reaction mixture was filtered to remove a small amount of precipitate from the solution. To the obtained solution was added sufficient ethanol to give a white solid with stirring. After filtering and drying, the resulting solid was purified further by fractional precipitation from DMSO by adding increasing amounts of ethanol to afford 5.5 g (68% yield) of HPB—SO$_3$Na. To purify the product further, the obtained solid was reprecipitated from a mixture of DMF and water and acidified with aqueous hydrochloric acid. Finally, the desired product was obtained by precipitation from a mixture of methanol and acetone. $^1$H NMR (D$_2$O): δ 7.41 (d, ortho-proton to the sulfonyl group, 12H), 7.17 (d, meta-proton to the sulfonyl group, 12H). $^{13}$C NMR (D$_2$O): δ 142.78(C—SO$_3$Na), 140.32 (para-carbon atom to the sulfonyl group) 139.74 (core phenyl group-C of the substituted phenyl group), 131.91(ortho-carbon atom to the sulfonyl group), 124.40 (meta-carbon atom to the sulfonyl group.

Example 2

Protein Separation by Displacement Anion Exchange Chromatography

Materials: Source 15Q Quaternary ammonium strong anion exchange columns, (15 μm, 100×4.6 mm i.d) was donated by Amersham Pharmacia Biotech (Uppsala, Sweden). ToyoPearl Super Q 650S (35 μm) and Q Sepharose HP Bulk stationary phase materials were donated by TOSOH BIOSEP (Montgomeryville, Pa., USA) and Amersham Biosciences (Uppsala, Sweden), respectively. Protein-Pak Q-8HR anion exchange (100×5 mm i.d) column was a gift from Waters Corporation (Milford, Mass., USA). TSK-Gel G3000SWXL size exclusion column (300 m×7.8 mm i.d.) and the TSK-Gel SWXL (40×6 mm i.d) guard column were gifts from TOSOH BIOSEP (Montgomeryville, Pa., USA). Q Sepharose HP and ToyoPearl Super Q 650S stationary phases were slurry packed in 100×5 mm I.D. and 50×5 mm I.D. columns, respectively. Tris(hydroxymethyl)amino methane, Tris(hydroxymethyl)amino methane hydrochloride, sodium chloride, sodium nitrate, human serum albumin (HSA), bovine serum albumin (BSA), α-lactalbumin, β-lactoglobulin A and β-lactoglobulin B from Sigma Chemical Company (St. Louis, Mo., USA). Pentaerythrityltetrabromide was purchased from Aldrich Chemical Company (Milwaukee, Wis., USA) and recrystallized from N,N-dimethylformamide (DMF) before use. N,N-Dimethylethanolamine was dried over solid NaOH and distilled under vacuum prior to use. 2-[2-(Dimethylamino) ethoxy]ethanol was dried and stored over molecular sieve (4A). N,N-Bis(3-aminopropyl) ethylenediamine was dried over solid NaOH, distilled under vacuum and stored over molecular sieve (4A). Anhydrous N,N-Dimethylformamide and dimethylsulfoxide (DMSO), tetrahydrofuran (THF) and ethanol from the Aldrich Chemical Company (Milwaukee, Wis., USA) were employed without further purification. All other solvents and reagents were used without additional purification unless specified in the procedure. The membranes for dialysis were purchased from Spectrum Medical Industries, Inc (Houston, Tex., USA) with molecular-weight-cut-off (MWCO) of 500 and from Membrane Filtration Products, Inc (Seguin, Tex., USA) with MWCO of 1000.

Instrumentation and Apparatus: Linear gradients were run on a Pharmacia fast protein liquid chromatographic (FPLC) system consisting of two P-500 pumps and a LCC-500 controller donated by Amersham Biosciences (Uppsala, Sweden). Displacement experiment was carried out using a Waters 590 HPLC pump (Waters, Milford, Mass.) connected to a chromatography column via a Model C10W port valve (Valco, Houston, Tex.). The column effluent was monitored using a Waters 484 UV-Vis absorbance detector (Waters Corporation, Milford, Mass., USA) and the data was acquired using a QuickLog (Version 1.4) chromatography workstation (Strawberry Tree, Inc., Sunnyvale, Calif., USA). Column effluent fractions during displacement experiment were collected using a LKB 2212 Helirac fraction collector (LKB Bromma, Sweden). Analysis of fractions collected during displacement experiments were carried out using a Waters 600 multisolvent delivery system, a Waters 712 WISP autoinjector and a Waters 484 UV-VIS absorbance detector controlled by a Millenium chromatography software manager (Waters, Milford, Mass.). $^1$H and $^{13}$C NMR spectra were recorded as ppm values with a 500 MHz Varian Unity-500 spectrometer. Infrared spectra were obtained on KBr pellets with a Perkin Elmer (Wellesley, Mass., USA) Paragon 1000 FT-IR. GC-MS spectra were obtained at injection temperatures of 250° C. and 280° C. with GC-17A and GCMS-QP5000 instruments from the Shimadzu Company (Kyoto, JAPAN). Melting points were measured on a differential scanning calorimeter (DSC) from Perkin Elmer (Wellesley, Mass., USA) model DSC 7 at a heating rate of 10° C./min under nitrogen.

Determination of Steric Mass Action (SMA) Parameters: SMA parameters were determined according to the procedure described by Brooks et al., AIChe J. 38, 1969 (1992). The SMA parameters were used to generate dynamic affinity plots for predicting the relative affinity of the displacers (Shukla, A A, et al., Ind. Eng. Chem. Res., 37, 4090 (1998)). For the displacers, linear gradient experiments were carried out at different times between buffer A (50 mM Tris, pH 7.5) and buffer B (50 mM Tris, pH 7.5, containing 2.5 M NaCl). Experiments were performed at 0.5 ml/min for Q Sepharose HP and Source 15Q, and at 0.4 ml/min for ToyoPearl Super Q-650S. Ion capacities (Λ) of the stationary phases were determined using a frontal method. The column was perfused with at least two different concentrations of sodium nitrate solutions in the equilibration buffer (50 mM Tris, 30 mM NaCl, pH 7.5). After each frontal, the stationary phases were regenerated using 2M NaCl solution. The breakthrough volumes of the sodium nitrate were used to calculate the ionic capacity of the stationary phases.

Displacer analysis: UV-VIS absorbance was used to monitor the column effluent during linear gradient analysis of the displacers. For displacer ICPSNA3, the effluent was monitored at 215 nm. For the remaining displacers, the effluent was monitored at 254 nm.

Figure 2:
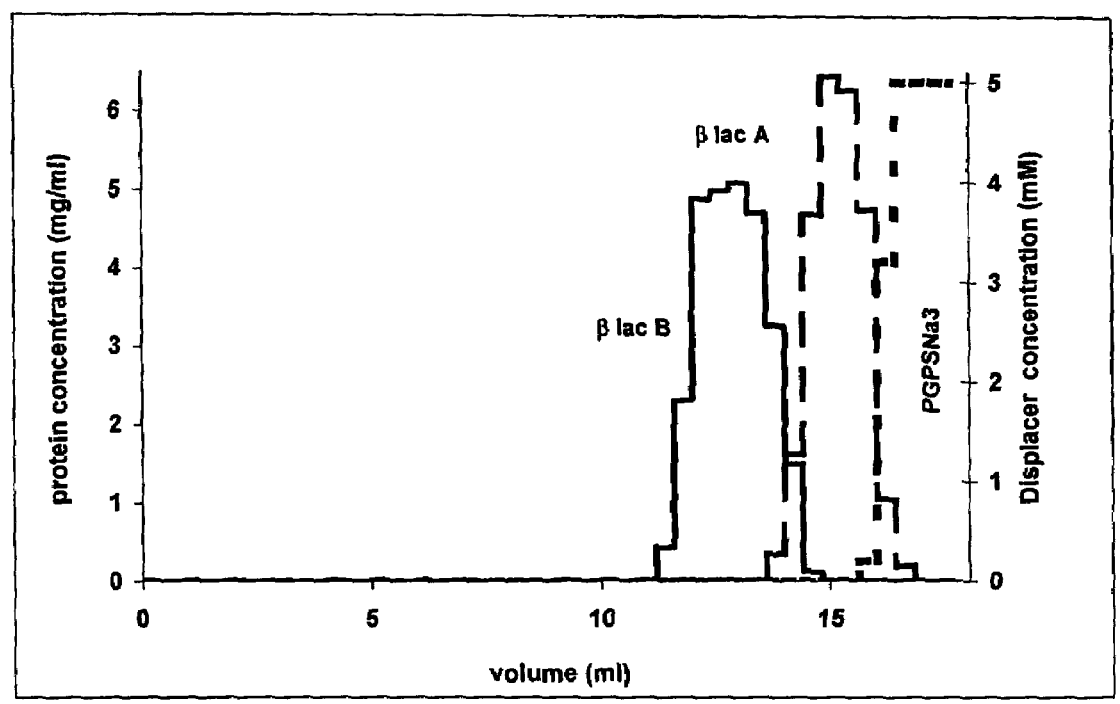
FIG. 2 shows displacement separation of a mixture of β-lactoglobulin A and β-lactoglobulin using PGPSNa₃ as a displacer.

Displacement Chromatographic Separation: For the displacement experiment, a Source 15Q (50×5 mm i.d.) the column was initially equilibrated with the carrier buffer 20 mM Tris+55 mM NaCl and then sequentially perfused with feed, displacer and regenerant solutions. The feed solution of 15.1 mg of β-lactoglobulin A and 16.7 mg of β-lactoglobulin B was prepared in 8 ml of carrier buffer. The protein solution (18 mg) was purified using 5 mM PG-PSNa$_3$ as the displacer. Appropriate fractions (400 μl) of column effluent were collected during the displacement experiments for subsequent analysis of proteins and displacer. The displacement experiment was carried out at a flow rate of 0.2 ml/min and the effluent was monitored at 235 nm. The column was regenerated sequentially with five column volumes of 2.5 M NaCl and 1 M NaOH solutions. Results are shown in FIG. 2.

Quantitative protein analysis of the fractions collected during the displacement experiment was performed by anion exchange chromatography under isocratic elution conditions. The proteins were analyzed using a Protein-Pak Q-8HR anion exchange (100×5 mm i.d) column with 170 mM NaCl in 20 mM Tris-HCl, pH 7.5. 5 μl samples were injected at a flow rate of 0.5 ml/min and the effluent was monitored at 235 nm.

Quantitative displacer analysis was performed by size exclusion chromatography using a TSK-Gel G3000SWXL (300 m×7.8 mm i.d.) in the presence of TSK-Gel SWXL (40×6 mm i.d) guard column. 5 μl samples were injected at a flow arte of 1 mL/min, 50 mM phosphate+100 mM NaCl, pH 6.0 as the carrier buffer. The effluent was monitored at 235 nm.

A common feature of these displacer molecules is that they all have a ring structure in the core of the molecule. Table 1 shows some of the structural characteristics of these displacers. To classify these molecules according to their hydrophobicity, log P (octanol/water partition coefficient) calculations were performed using MOE software (Chemical Computing Group, Inc., Canada). To obtain other properties of these molecules, the same software was employed to calculate the 2D and 3D descriptors. The properties summarized in Table 1 enabled us to divide these molecules into two groups. The first group includes the molecules with more than one ring: HPB—SO$_3$Na, PG(E01)PhSO$_3$Na and TA-PhSO$_3$Na. It should also be mentioned that when the number of aromatic rings on the displacers in this group was increased, these moieties were added to the termini of the chains attached to the core ring structure. Hydrophobicity is another significant property of the displacers that constitute the first group. The remaining molecules with only the core ring form the second group. We can summarize the important properties of these homologous series of molecules as follows: According to Table 1, the most hydrophobic displacer and the displacer with the most aromatic rings was HPB—SO$_3$Na. PG(E01)PSNa$_3$ and PG(E01)PhSO$_3$Na are different because the latter has 3 more aromatic rings at the termini as is the case for TaPSNa$_3$ and TaPhSO$_3$Na. ICP-SNa$_3$ was the only displacer without any aromatic ring. PGPSNa$_3$ and TaPSNa$_3$ were different from each other in terms of the type of the aromatic ring they contain, benzene and triazine, respectively.

TABLE 1

Properties of the displacers

| Molecule | MW | FCharge[1] | b_ar[2] | LogP (o/w)[3] | # of rings[4] | a_acc[5] |
|---|---|---|---|---|---|---|
| HPB-SO$_3$Na | 1146.9 | −6 | 42 | 6.736 | 7B | 0 |
| PG(E01)Ph-SO$_3$Na | 792.7 | −3 | 24 | 2.397 | 4B | 6 |
| TA-PhSO$_3$Na | 663.5 | −3 | 24 | 0.946 | 3B + 1T | 6 |
| PG(E01)PSNa$_3$ | 690.6 | −3 | 6 | −1.350 | 1B | 6 |
| PG-PSNa$_3$ | 558.5 | −3 | 6 | −0.362 | 1B | 3 |
| TA-PSNa$_3$ | 561.4 | −3 | 6 | −2.804 | 1T | 6 |
| IC-PSNa$_3$ | 561.4 | −3 | 0 | −2.855 | 1T | 0 |

[1]Fcharge: Formal charge on the molecule
[2]b_ar: number of aromatic bonds
[3]logP(o/w): octanol/water partition coefficient
[4]B = benzene, T = triazine
[5]a_acc: number of hydrogen-bond acceptor atoms The linear SMA parameters of the displacer molecules were determined on each stationary phase, as described in the experimental section, and the values are shown in Table 2. The parameters for PG(E01)Ph—SO$_3$Na could not be obtained because the displacer had such a high affinity that it didn't elute from any of the stationary phases under the experimental conditions. As shown in the Table, there were significant differences in the values of these parameters as the stationary phase and/or the displacer compound was changed. For example, the characteristic charges were slightly higher on the Source 15Q resin, than for the other two resins which indicates that most of the charged groups on the displacers were effectively interacting with the charged sites on this stationary phase. The equilibrium constant (K) values were also slightly higher on Source 15Q resin especially for HPB—SO$_3$Na and TA-PhSO$_3$Na, which indicates that, in general, the displacers were bound more strongly to the resin. These results demonstrate that the mode of interaction and the strength of binding can be affected by both displacer and stationary phase chemistry.

TABLE 2

Linear SMA parameters of the displacers on different stationary phases

| Stationary Phase | Q Sepharose HP | | Source 15Q | | ToyoPearl SuperQ-650S | |
|---|---|---|---|---|---|---|
| Displacer | v | K | v | K | v | K |
| HPB-SO3Na | 4.11 | 102.0 | 4.36 | 478.0 | 3.76 | 54.8 |
| TA-PhSO3Na | 2.22 | 29.00 | 1.9 | 169.0 | 1.67 | 83.7 |
| PG-PSNa3 | 2.18 | 1.59 | 3.04 | 9.93 | 2.54 | 2.61 |
| TA-PSNa3 | 2.81 | 0.416 | 3.02 | 1.18 | 2.69 | 0.39 |
| PG(E01)PSNa3 | 2.55 | 0.374 | 2.56 | 3.12 | 2.61 | 0.454 |
| IC-PSNa3 | 2.54 | 0.352 | 3.07 | 3.21 | 2.7 | 0.040 |

By evaluating the dynamic affinity of these displacer molecules, we could examine the relative affinities that would be expected under the non-linear binding conditions found in displacement chromatography. Dynamic affinity plots are log—log plots and thus only significant changes in the dynamic affinities will be observed. Further, while the value of log (K) will affect the general location of the dynamic affinity lines, only the characteristic charge affects the slope of these lines.

The Q Sepharose HP medium is composed of a rigid cross-linked agarose. Agarose is an example of a polysaccharide stationary phase material, which has a high degree of hydrophilicity because of the presence of a high density of free OH groups. It is an alternating copolymer of (1–3)-b-D-galactopyranose and (1–4)-3,6-anhydro-a-L-galactopyranose and is hydrophilic. A functional group (quaternary ammonium) is added to the saccharides through a —CO—NH—CH—O grouping.

It was observed that the molecules belonging to the first group (>/ring) had higher affinities on the Q Sepharose HP stationary phase. The order for the first group was: PG(E01)PhSO$_3$Na>HPB—SO$_3$Na>TA-PhSO$_3$Na. One possible reason for PG(E01)PhSO$_3$Na having a very high affinity could be the longer chains attached to the middle aromatic ring which will possibly make the molecule more flexible than the other displacers found in this group because the flexibility will enable it to interact with the backbone matrix. The second group followed the order of PG-PSNa$_3$>TAPSNa$_3$>PG(EO1)PSNa$_3$=IC—PSNa$_3$. Even though they all have similar characteristic charges, PG-PSNa$_3$ has one aromatic ring that apparently makes it superior to the other molecules in this group. However, having one aromatic group like PG-PSNa$_3$, PG(E01)PSNa$_3$ has the lowest affinity in this group. Log P values indicate that PGPSNa$_3$ (log P=−0.362) is more hydrophobic than PG(E01)PSNa$_3$ (log P=−1.35), which may have caused the difference in their efficacy for the agarose-based resin. Affinity ranking plots have also shown that PGPSNa$_3$ binds more strongly than TAPSNa$_3$, which is indicative of the higher efficacy of benzene rings over triazine rings. It also indicates that even though TAPSNa$_3$ has more hydrogen bonding capability than PGPSNa$_3$, aromaticity dominates the mode of interaction on the agarose resin. IC—PSNa$_3$ has the lowest affinity, which clearly shows that having no aromatic rings has a significant impact on lowering the efficacy of the displacer. In addition, the difference in the affinity of the first group and second group of displacers was more pronounced than it was for the other stationary phases. The SMA parameters indicate that all the molecules have a characteristic charge in the range of 2–3 with the exception of HPB—SO$_3$Na, which has a characteristic charge of 4.11.

Source 15Q is a hydrophilized PS-DVB resin used for protein chromatography. FIG. 1 shows the dynamic affinities of the displacers for the Source 15Q stationary phase. As for the Q Sepharose HP stationary phase, the displacers in the first group have higher affinity than the displacers in the second group. The order of affinity in the first group is: PG(E01)PhSO$_3$ [not shown]>TAPhSO$_3$Na>HPB—SO$_3$Na. Even though the dynamic affinity line of TAPhSO$_3$Na lies above HPBSO$_3$Na, we have to make clear that the former displacer has a lower characteristic charge, which causes the dynamic affinity line to be steeper. However, HPB—SO$_3$Na has a shallower line (high v and K), which indicates that this displacer will be more effective over a wide range of operating conditions. The order of dynamic affinity for the second group was PGPSNa$_3$>ICPSNa$_3$=PG(E01)PSNa$_3$>TAPSNa$_3$. Similarly to the previous stationary phase, PGPSNa$_3$ with one benzene ring has superior affinity to the other displacers with no aromatic rings or a triazine ring. In general, the equilibrium constants obtained on this stationary phase were higher than they were for the other resins, which was indicative of stronger binding. This result could be due to the aromatic ring content of this resin (PS/DVB), which will contribute strongly to the π—π interactions. In contrast to Q Sepharose HP, the affinity differences between the first and second group displacers were not as pronounced for this stationary phase. As with the previous resin, aromaticity/hydrophobicity was still the dominating secondary interaction in increasing the efficacy of displacers on the hydrophilized PS/DVB Source 15Q resin.

ToyoPearl Super Q-650S ion exchangers consist of a poly(methyl)methacrylate backbone bearing quaternary ammonium groups. Dynamic affinities of the displacers were determined for this stationary phase. As before, the dynamic affinity lines for the first group with a high number of aromatic rings lie above the second group of displacers. The order of affinity for the first group of displacers was: PG(E01)PhSO$_3$Na>TaPhSO$_3$Na>HPB—SO$_3$Na. Once again, because of the shallower dynamic affinity line, HPB—SO$_3$Na will be more effective over a range of operating conditions. The order of dynamic affinity for the second group of displacers was: PGPSNa$_3$>TAPSNa$_3$=PG(E01)PSNa$_3$>ICPSNa$_3$. The benzene ring was significantly more efficacious than the triazine ring, which was true for all of the stationary phases, employed for this study. It was demonstrated that aromaticity is very significant in increasing the efficacy of the displacers on the poly(methyl)methacrylate resins.

In addition to obtaining SMA parameters for the various displacers, we also obtained SMA parameters for a set of proteins on Source 15Q stationary phase. The set consisted of proteins that have been employed commonly in the literature to demonstrate the efficiency of anion exchange resins for protein purifications. It was clear that all of the displacers synthesized for this study had dynamic affinities greater than the proteins in this set. This result indicated that the anion exchange displacement experiments that would be carried out using these displacers may be effective for very challenging protein purifications (e.g. HSA and BSA, β-lactoglobulin A and β-lactoglobulin B). As seen in FIG. 2, displacement separation of β-lactoglobulins was successfully carried out using PGPSNa$_3$ as a displacer.

In addition, the use of very low concentrations of very high affinity displacers, such as HPBSO$_3$Na, in an anion exchange displacement chromatographic purification may result in very high resolution protein separations.

The common trend for all of the resins employed for this study was that the displacers with a high degree of aromaticity (increasing number of aromatic bonds) had very high affinities. For Q Sepharose HP and ToyoPearl SuperQ-650S, the displacer without any aromatic bonds (IC—PSNa$_3$) had the least affinity. Furthermore, the results indicated that benzene rings were superior to triazine rings in increasing the affinity for anion exchange systems. The affinity differences between the first and second group of displacers were much more pronounced on Q Sepharose HP resin. In all cases, HPSO$_3$Na with the shallower dynamic affinity line was shown to be efficacious over a wide range of operating conditions. As analyzed for the Source I SQ stationary phase, all the displacers synthesized in this work can be employed for the purification of very challenging protein mixtures.

Example 3

High Throughput Screening of Displacers for the Purification of Oligonucleotides Materials: Bulk strong anion exchange (quaternary ammonium), Source 30Q (30 μm) was kindly donated by Amersham Biosciences (Uppsala, Sweden). Poros HQ/H (10 μm), 100×4.6 mm I.D. was obtained from Perseptive Biosystems (Framingham, Mass., USA).

Apparatus: Oligonucleotide analysis was carried out using a Waters 600 multisolvent delivery system, a Waters 712 WISP autoinjector and a Waters 484 UV-Vis absorbance detector controlled by a Millenium chromatography manager (Waters, Milford, Mass., USA).

Procedure: The bulk stationary phase (Source 30Q; 1.8 ml) was first washed with deionized water and then the mobile phase buffer, 20 mM NaOH+500 mM NaCl was added and allowed to equilibrate for 2 hours. After gravity settling of the stationary phase, the supernatant was removed and 21 ml of 15 mg/ml phosphorothioate anti-sense oligonucleotide in the mobile phase buffer was then added and equilibrated in a shaker for 12 hours at 23° C. The supernatant was then analyzed by high temperature (70° C.) anion exchange chromatography to determine the oligonucleotide concentration and the amount adsorbed on the stationary phase was calculated through a mass balance. The supernatant was then removed and 25 μl aliquots of the stationary phase with adsorbed oligonucleotide were added to separate vials. Aliquots (300 μl) of 10 mM solutions of each displacer in the mobile phase buffer were then added to individual vials, and were allowed to equilibrate for 6 hours. After equilibration was complete, the stationary phase was allowed to gravity-settle and the supernatants were removed and analyzed to determine the percentage of oligonucleotide displaced by each displacer. These experiments were carried out in duplicate. Results appear in Table 3.

TABLE 3

HTS of Displacers for Oligonucleotides

| Displacer | % Oligos Displaced | | |
|---|---|---|---|
| | Average | Vial 1 | Vial 2 |
| Buffer Control | 1.9 | 2.1 | 1.7 |
| IC-PSNa$_3$ | 42.1 | 42.2 | 42.1 |
| TA-PSNA3 | 42.3 | 43.3 | 41.3 |
| PG(EO1)-PSNa$_3$ | 44.3 | 42.8 | 45.8 |
| PG-PSNa$_3$ | 46.8 | 46.4 | 47.2 |
| PG(EO1)-PhSO$_3$Na | 80.4 | 77.0 | 83.6 |

The results indicate that displacers of formula I can be effective in chromatographic separations of oligonucleotides. In particular, the compound that displaced the highest amount of oligonucleotide was PG(E01)-PhSO$_3$, which displaced 80% of the oligonucleotide from the stationary phase material.

The invention claimed is:

1. A method for separating one or more components of a biomolecule mixture by means of an ion exchange chromatographic system operated in the displacement mode, said method comprising sequentially perfusing the system with a first solution comprising the biomolecule mixture, and a second solution comprising a displacer of structure

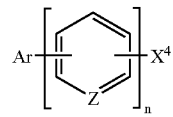

wherein

Ar is phenyl, naphthalenyl, phenanthrenyl, anthracenyl, perylenyl, pyrenyl, fluorenyl, triazolyl, carbazolyl, indolyl, benzocarbazolyl, acridinyl, phenothiazinyl, or thianthrenyl;

$X^4$ is sulfonate, sulfate, phosphate, carboxylate, tertiary amino or quaternary amino;

Z is CH or N; and n is an integer from 1 to 6.

2. A method according to claim 1, wherein the displacer is an anion.

3. A method according to claim 1, wherein the displacer is a cation.

4. A method according to claim 1, wherein the biomolecule mixture comprises at least one protein.

5. A method according to claim 1, wherein the biomolecule mixture comprises at least one oligonucleotide.

6. A method according to claim 1, additionally comprising equilibrating the system with a carrier solution before sequentially perfusing the system with the first solution.

7. A method according to claim 1, additionally comprising regenerating the system after perfusing the system with the second solution.

8. A method according to claim 1, wherein Ar is phenyl.

9. A method according to claim 1, wherein Ar is triazolyl.

10. A method according to claim 1, wherein the displacer is

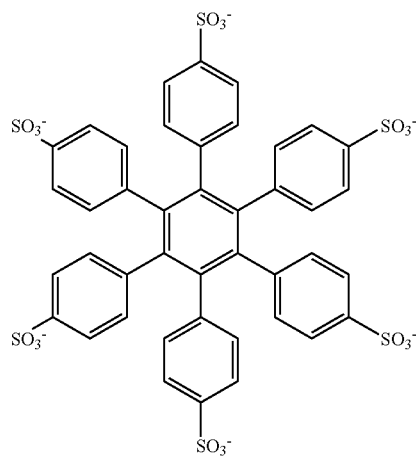

* * * * *